United States Patent
Yu et al.

(10) Patent No.: US 11,314,096 B2
(45) Date of Patent: Apr. 26, 2022

(54) SYSTEMS AND METHODS FOR AIRY BEAM OPTICAL COHERENCE TOMOGRAPHY

(71) Applicant: The Curators of the University of Missouri, Columbia, MO (US)

(72) Inventors: Ping Yu, Columbia, MO (US); Lixin Ma, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 398 days.

(21) Appl. No.: 16/446,916

(22) Filed: Jun. 20, 2019

(65) Prior Publication Data

US 2019/0302465 A1 Oct. 3, 2019

Related U.S. Application Data

(63) Continuation of application No. PCT/US2017/067881, filed on Dec. 21, 2017.
(Continued)

(51) Int. Cl.
*G02B 27/09* (2006.01)
*A61B 3/10* (2006.01)
(Continued)

(52) U.S. Cl.
CPC .......... *G02B 27/0955* (2013.01); *A61B 3/102* (2013.01); *A61B 5/0066* (2013.01);
(Continued)

(58) Field of Classification Search
CPC ............ G02B 27/0955; G02B 27/0927; G02B 27/0988; G02B 27/283; G02B 26/105;
(Continued)

(56) References Cited

U.S. PATENT DOCUMENTS 4,053,905 A * 10/1977 Schlater ................ H01J 9/2272
396/547
8,101,929 B1   1/2012 Christodoulides et al.
(Continued)

FOREIGN PATENT DOCUMENTS

CN   205620619 U  * 10/2016
CN   205620619 U    10/2016

OTHER PUBLICATIONS

Notification of Transmittal of the International Search Report and the Written Opinion of the International Searching Authority, or the Declaration dated May 31, 2018; International Application No. PCT/US2017/067881; International Filing Date: Dec. 21, 2017; Applicant: The Curators of the University of Missouri.

*Primary Examiner* — Collin X Beatty
(74) *Attorney, Agent, or Firm* — Erise IP, P.A.

(57) ABSTRACT

A system and method for performing Optical Coherence Tomography on a sample utilizes collimated, phase modulated beams of light in an interferometer. At least one of the beams of light utilized exists as an Airy beam for at least a portion of the procedure, obviating any deleterious impact caused by the Gaussian beam diffraction. The system may incorporate a light source, polarization beam splitter, delay line, non-polarization beam splitters, lenses, phase masks, waveplates, and mirrors, any or all of which may be controlled by a computing element.

20 Claims, 9 Drawing Sheets

Related U.S. Application Data (60) Provisional application No. 62/437,130, filed on Dec. 21, 2016.

(51) Int. Cl.
| | |
|---|---|
| *G01B 9/02* | (2006.01) |
| *G02B 26/10* | (2006.01) |
| *G02B 27/28* | (2006.01) |
| *A61B 5/00* | (2006.01) |
| *G01B 9/02015* | (2022.01) |
| *G01B 9/02091* | (2022.01) |

(52) U.S. Cl.
CPC .............. *A61B 5/0073* (2013.01); *G01B 9/02* (2013.01); *G01B 9/02015* (2013.01); *G01B 9/02091* (2013.01); *G02B 26/105* (2013.01); *G02B 27/0927* (2013.01); *G02B 27/0988* (2013.01); *G02B 27/283* (2013.01); *G01B 2290/70* (2013.01)

(58) Field of Classification Search
CPC ..... A61B 3/102; A61B 5/0066; A61B 5/0073; G01B 9/02; G01B 9/02015; G01B 9/02091; G01B 2290/70
USPC ........................................................ 351/215
See application file for complete search history.

(56) References Cited

U.S. PATENT DOCUMENTS

| | | | |
|---|---|---|---|
| 2010/0067020 A1 | 3/2010 | Podoleanu | |
| 2011/0058175 A1* | 3/2011 | Suehira | A61B 3/102 356/450 |
| 2012/0051375 A1* | 3/2012 | Karpushko | H01S 3/109 372/22 |
| 2019/0170695 A1* | 6/2019 | Xiang | G01N 21/1702 |

\* cited by examiner

Fourier Transform

SYSTEMS AND METHODS FOR AIRY BEAM OPTICAL COHERENCE TOMOGRAPHY

RELATED APPLICATIONS

The present application is a continuation application of International Application No. PCT/US2017/067881, filed Dec. 21, 2017, which claims priority to U.S. Provisional Patent Application No. 62/437,130, filed Dec. 21, 2016. The above referenced applications are hereby incorporated by reference into the present application in their entirety.

FIELD

Embodiments of the invention are broadly directed to systems and methods of performing Optical Coherence Tomography using an Airy beam. More specifically, embodiments of the invention apply an Airy beam to produce a three-dimensional image of optical scattering within a sample with an increased depth of field.

RELATED ART

Optical Coherence Tomography (OCT) utilizes broadband light sources or swept source lasers to create cross-sectional images of a sample using low-coherence interferometry. This is achieved by measuring the interferograms or spectral interferograms of the sample beam reflected from sub-surface structures within the sample and the reference beam light that has not been reflected from the sample when the optical path length differences between the sample and reference are less than the coherence length of the light source. Due to the scale and noninvasive nature of the procedure, OCT is particularly useful for imaging biological tissues. As such, systems performing OCT are being used in the fields of ophthalmology, cardiology, gastroenterology, dermatology etc., primarily as a diagnostic tool.

Typical systems and methods for OCT employ a collimated Gaussian beam generated from within a single mode fiber, which is then focused with a lens onto a very small area on a surface of a sample. Because the beam's size on the surface of the sample will determine a lateral resolution of a produced image, focusing of the beam is desirable.

Conventional methods of OCT that image a sample using a Gaussian beam are undesirably limited in the imaged depth of field that they are capable of producing. This is because a Gaussian beam diffracts (spreads) as it propagates, resulting in a loss of beam intensity and lateral resolution with distance. The lens necessary for the lateral resolution, described above, exacerbates diffraction of Gaussian beams in OCT. Hence, a focused Gaussian beam in an OCT system has a very small (~1.7 mm) depth of field in the imaged sample (supposing, for instance, the center wavelength of 930 nm and the Gaussian beam waist of 16 µm). Here the beam waist is defined as the full width at half maximum (FWHM) of the Gaussian beam at the focal point of the lens. In many pursuits, a 1.7 mm depth of field is insufficiently shallow to completely understand structures of interest. In particular, the depth of field desired for many ophthalmological diagnostic-imaging procedures is an order of magnitude greater than is currently available, roughly more than 10 mm.

Another example of limited depth of field is ultra-high resolution OCT or OCM. In this case, a tightly focused Gaussian beam is used. If the waist of Gaussian beam is about 3 µm, the depth of field will be 61 µm for the center wavelength of 930 nm. This depth of field may not suffice for many diagnostic applications.

Elimination of the deleterious impact of diffraction of Gaussian beams on OCT imaging would result in a stark increase in depth of field, possibly even greater than the ten-fold increase desired. OCT systems and methods configured to negate beam diffraction would provide a clearer picture to scientists and healthcare providers of the internal microstructures of a sample, supporting and improving research, diagnostics, and treatment.

SUMMARY

Embodiments of the invention provide systems and methods for performing OCT using an Airy beam, such that beam diffraction is negated. A first embodiment of the invention is directed to a method of performing Optical Coherence Tomography on a sample including the steps of generating a source beam, splitting the source beam into a signal beam and a reference beam using a non-polarization beam splitter, converting the signal beam into an Airy beam, directing the signal beam towards the sample using scanning mirrors, and combining the signal beam and the reference beam into a combined beam using the same non-polarization beam splitter. The combined beam may be detected by a detection unit and processed in a graphics processing unit. The signal beam may be converted to an Airy beam using a phase mask and at least one lens.

A second embodiment of the invention is directed to an Optical Coherence Tomography system comprising a source beam, first and second non-polarization beam splitters, a polarization beam splitter, first and second half-wave plates, a quarter-wave plate, first and second phase masks, a first lens, second and third lenses, a mirror, and scanning mirrors. The first non-polarization beam splitter splits the source beam into a signal beam and a reference beam. The first phase mask and first lens convert the signal beam to an Airy beam. The scanning mirrors may comprise one mirror, two mirrors, or more driven by servos coupled to a galvanometer, which is configured to direct the signal beam towards a sample. The first half-wave plate and the quarter-wave plate change the polarization of the signal beam, while the second half-wave plate changes the polarization of the reference beam. The second phase mask modulates the phase of the reference beam. The second non-polarization beam splitter combines the signal beam and reference beam into a combined beam and directs the combined beam towards a detection unit.

A third embodiment of the invention is directed to an Optical Coherence Tomography imaging system comprising a source beam, first and second non-polarization beam splitters, a polarization beam splitter, a phase mask, a first lens, first and second half-wave plates, a quarter-wave plate, a mirror, and scanning mirrors. The first non-polarization beam splitter splits the source beam into a reference beam and a signal beam, while the second non-polarization beam splitter later combines the reference beam and signal beam into a combined beam. The phase mask is placed before the polarization beam splitter. The phase mask and first lens convert the signal beam to an Airy beam to be scanned across a sample via the scanning mirror. The scanning mirrors may comprise two mirrors driven by servos coupled to a galvanometer.

This summary is provided to introduce a selection of concepts in a simplified form that are further described below in the detailed description. This summary is not intended to identify key features or essential features of the claimed subject matter, nor is it intended to be used to limit the scope of the claimed subject matter. Each of the above embodiments may include further lenses, mirrors, polarization and/or non-polarization beam splitters, phase masks, quarter-wave and/or half-wave plates, and delay lines. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Embodiments of the invention solve the above problems of conventional Optical Coherence Tomography (OCT) by providing systems and methods of performing OCT using an Airy beam. More specifically, embodiments of the invention include structures and methods for performing an OCT procedure using collimated, phase modulated beams of light in an interferometer, wherein at least one beam of light exists as an Airy beam for at least a portion of the procedure. The systems and methods described provide an increase in the depth of field of an imaged sample that may be particularly applicable to imaging of biological tissues, such as eyes, but this exemplary use is not intended to be limiting.

Figures 1A, 1B:
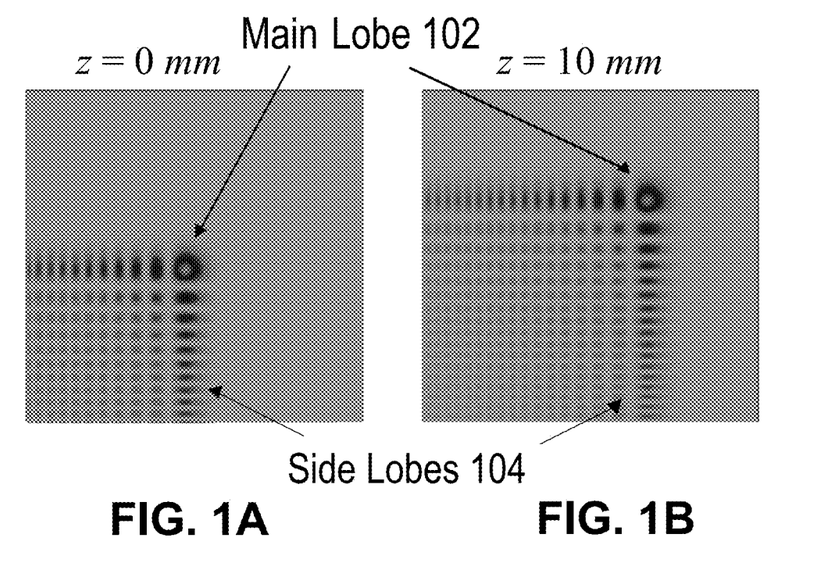
FIG. 1A is an intensity pattern defining an Airy beam at an origin.
FIG. 1B is an intensity pattern defining an Airy beam that has moved during a propagation of 10 mm from an origin.

FIG. 1A illustrates an intensity pattern defining an Airy beam at an origin (z=0 mm). The pattern comprises regularly spaced dark "spots," with the largest and darkest appearing at the upper right corner of the pattern. The spots become progressively smaller and fainter with increased distance from this darkest spot, known as a "main lobe."

FIG. 1B illustrates the same intensity pattern illustrated in FIG. 1A propagated forward in space by z=10 mm. The main lobe, again, appears at one corner of the pattern with many other smaller, fainter regularly spaced spots (the "side lobes"). The Airy beam moves towards upper right direction due to the lateral acceleration. There are more side lobes shown in FIG. 1B than in FIG. 1A because of a larger fiend of view for the Airy beam, but they continue to exhibit decreased size and intensity with distance from the main lobe.

In general, an Airy beam is a waveform (in this case, of light) that has an area of principal intensity (the "main lobe" described above) surrounded in one quadrant of the surrounding space by a series of "side lobes." As the waveform moves from z=0 mm in FIG. 1A to z=10 mm in FIG. 1B, the series of lobes expands out from its original position, which (as seen side-on) would appear to be freely accelerating in a parabolic arc. This is further illustrated in feature 202 of FIG. 2; the darkest portion of the waveform appears to curve upward as the wave propagates forward in space.

In actuality, an Airy beam is an interference pattern that propagates with a lateral acceleration as it travels along a straight path due to the Fourier transform of cubic phase pattern. The main lobe 102 and side lobes 104 are created at points of constructive interference of the Airy beam waveform, while the empty "gaps" in between occur at areas of total destructive interference. As the beam propagates forward (in the case of FIGS. 1A and B, along the z-axis), the lobes are repositioned in space due to the lateral acceleration. Thus, the beam of light itself does not change, and the points in the pattern at which constructive and destructive interference actually curve.

Figure 2:
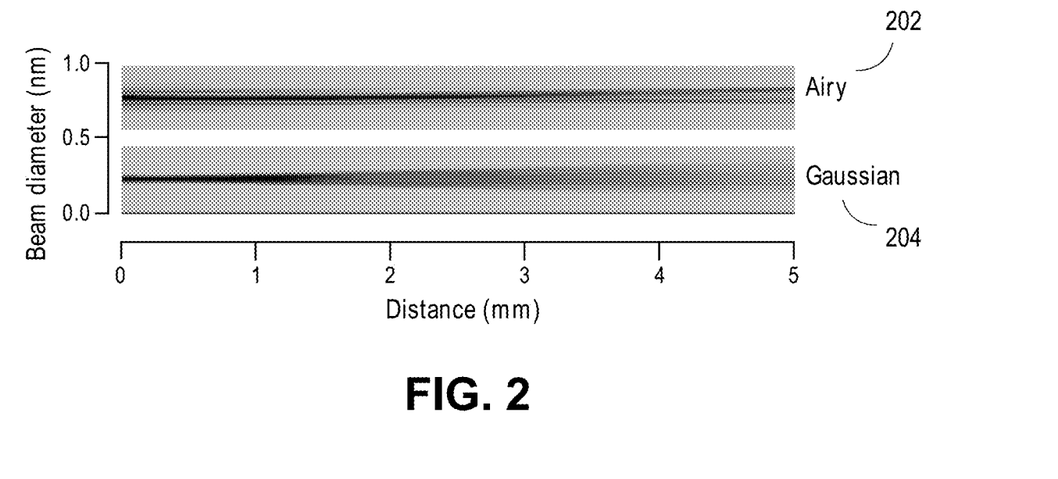
FIG. 2 is a comparison of the dependence beam diameters of an Airy beam and a Gaussian beam on propagation from an origin.

FIG. 2 illustrates a side-on comparison of a typical Gaussian beam 204 and an Airy beam 202 propagating along parallel paths. The horizontal z-axis represents the distance (in mm) propagated by each beam, while the vertical x-axis represents the lateral distance of each beam (again, in mm). The darkness of each beam represents its intensity at each point through which the given beam propagates.

Unlike a Gaussian beam, the main lobe of an Airy beam does not diffract as the waveform propagates through space. As seen in FIG. 2, a Gaussian beam 204 loses intensity with distance due to an increase in beam diameter, while an Airy beam's main lobe, the darkest portion of beam 202, maintains a constant diameter along a curved path. This property of Airy beams can be exploited to circumvent the depth of field limitation described above with respect to conventional OCT systems based on Gaussian beams. An OCT system wherein a sample is scanned using the main lobe of an Airy beam may generate an image with a depth of field on the order of approximately 10 mm.

Embodiments of the invention provide a method of imaging a sample by generating a source beam of light, splitting the source beam into signal and reference beams, converting the signal beam to an Airy beam, scanning the sample using one or more scanning mirrors, and combining the beams into a combined beam for detection. Embodiments of the invention may utilize a computer processor, memory, storage, graphics card, and/or other hardware to control the system and/or process information carried by the combined beam.

Embodiments further provide systems and methods for directing, focusing, phase modulating, and/or polarizing said beams. Embodiments of the invention may do so by including mirrors, lenses, phase masks, waveplates, polarizers, and/or beam splitters. Waveplates used may be half-wave plates and/or quarter-wave plates. Beam splitters used may be polarization beam splitters and/or non-polarization beam splitters. Embodiments of the invention may further or alternatively include one or more delay lines for performing Fourier-domain OCT or time-domain OCT, as further described below.

In some embodiments, one or more lenses may be used. The lenses may be partitioned into distinct segments, each of which focuses the light passing through to a common single focal point.

Embodiments of the invention further disclose systems and methods of generating one or more Airy beams. In some embodiments, an Airy beam may be generated by applying a phase mask into a collimated Gaussian beam and passing it through a specially-designed lens, which Fourier transforms the modulated Gaussian beam into an Airy beam. As further described below, a phase mask may be used to modulate the Gaussian beam in the reference to get another Airy beam.

Figure 3:
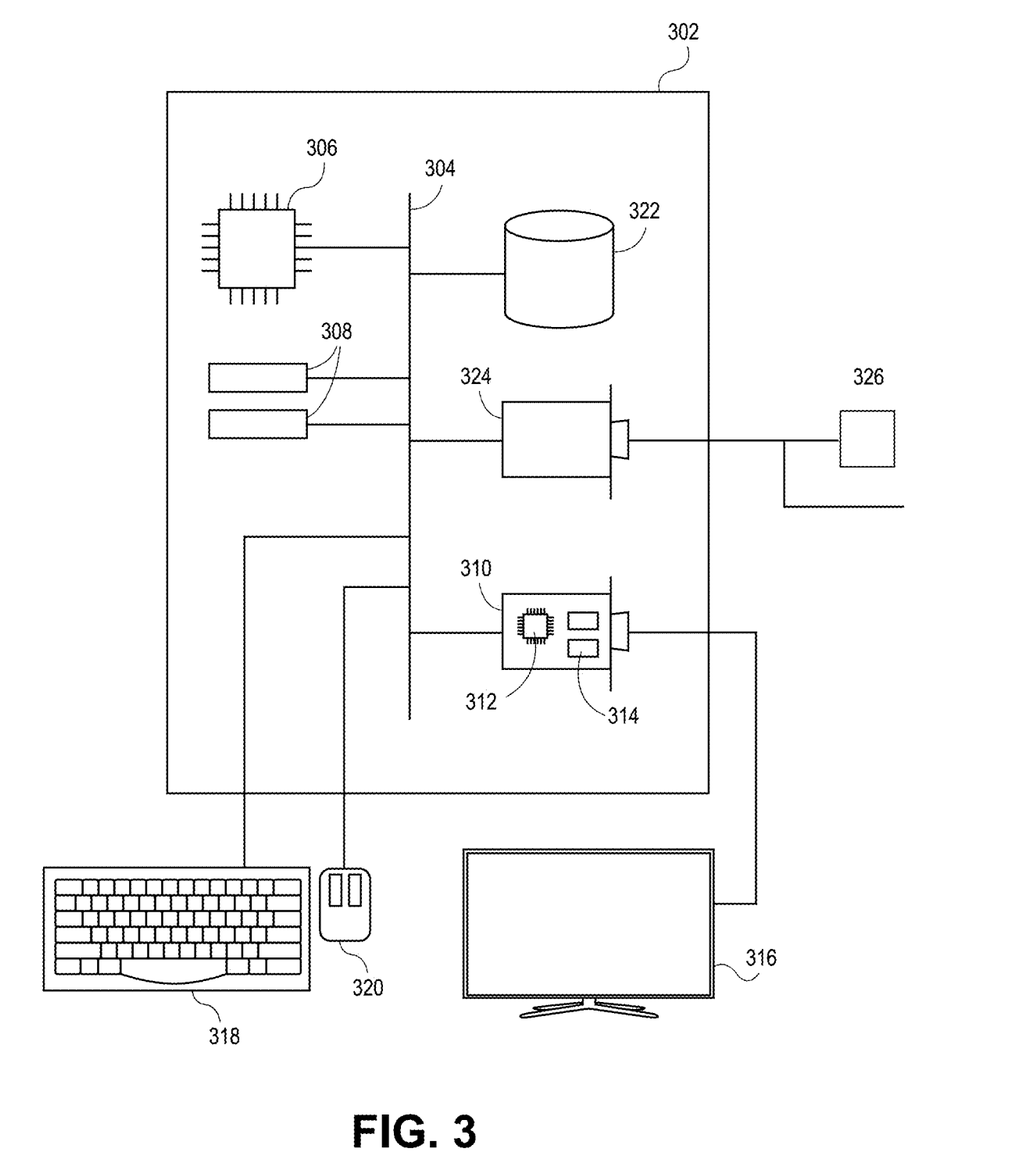
FIG. 3 is a schematic view of various computing components of an Optical Coherence Tomography system including a processor, a memory, a network interface card, and a detector.

Turning to FIG. 3, an exemplary hardware platform that can form one element of certain embodiments of the invention is depicted. Computer 302 can be a desktop computer, a laptop computer, a server computer, or any other form factor of general- or special-purpose computing device. Depicted with computer 302 are several components, for illustrative purposes. In some embodiments, certain components may be arranged differently or absent. Additional components may also be present. Included in computer 302 is system bus 304, whereby other components of computer 302 can communicate with each other. In certain embodiments, there may be multiple busses or components may communicate with each other directly. Connected to system bus 304 is central processing unit (CPU) 306. Also attached to system bus 304 are one or more random-access memory (RAM) modules 308. Also attached to system bus 304 is graphics card 310. In some embodiments, graphics card 304 may not be a physically separate card, but rather may be integrated into the motherboard or the CPU 306. In some embodiments, graphics card 310 has a separate graphics-processing unit (GPU) 312, which can be used for graphics processing or for spectral analysis. Also on graphics card 310 is GPU memory 314. Connected (directly or indirectly) to graphics card 310 is display 316 for user interaction. In some embodiments no display is present, while in others it is integrated into computer 302. Similarly, peripherals such as keyboard 318 and mouse 320 are connected to system bus 304. Like display 316, these peripherals may be integrated into computer 302 or absent. Also connected to system bus 304 is local storage 322, which may be any form of computer-readable media, and may be internally installed in computer 302 or externally and removeably attached.

Computer-readable media include both volatile and non-volatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 324 is also attached to system bus 304 and allows computer 302 to communicate over a network. NIC 324 can be any form of network interface known in the art, such as Ethernet, ATM, fiber, Bluetooth, or Wi-Fi (i.e., the IEEE 802.11 family of standards). NIC 324 may connect computer 302 to a local network, which may also include one or more other computers, hardware components, storage devices, servos, and/or detectors. In some embodiments, NIC 324 may connect computer 302 to a detector 326 such as a line scan camera. The local network may in turn connected to Internet, or in some embodiments computer 302 may itself be directly connected to Internet.

Figure 4A:
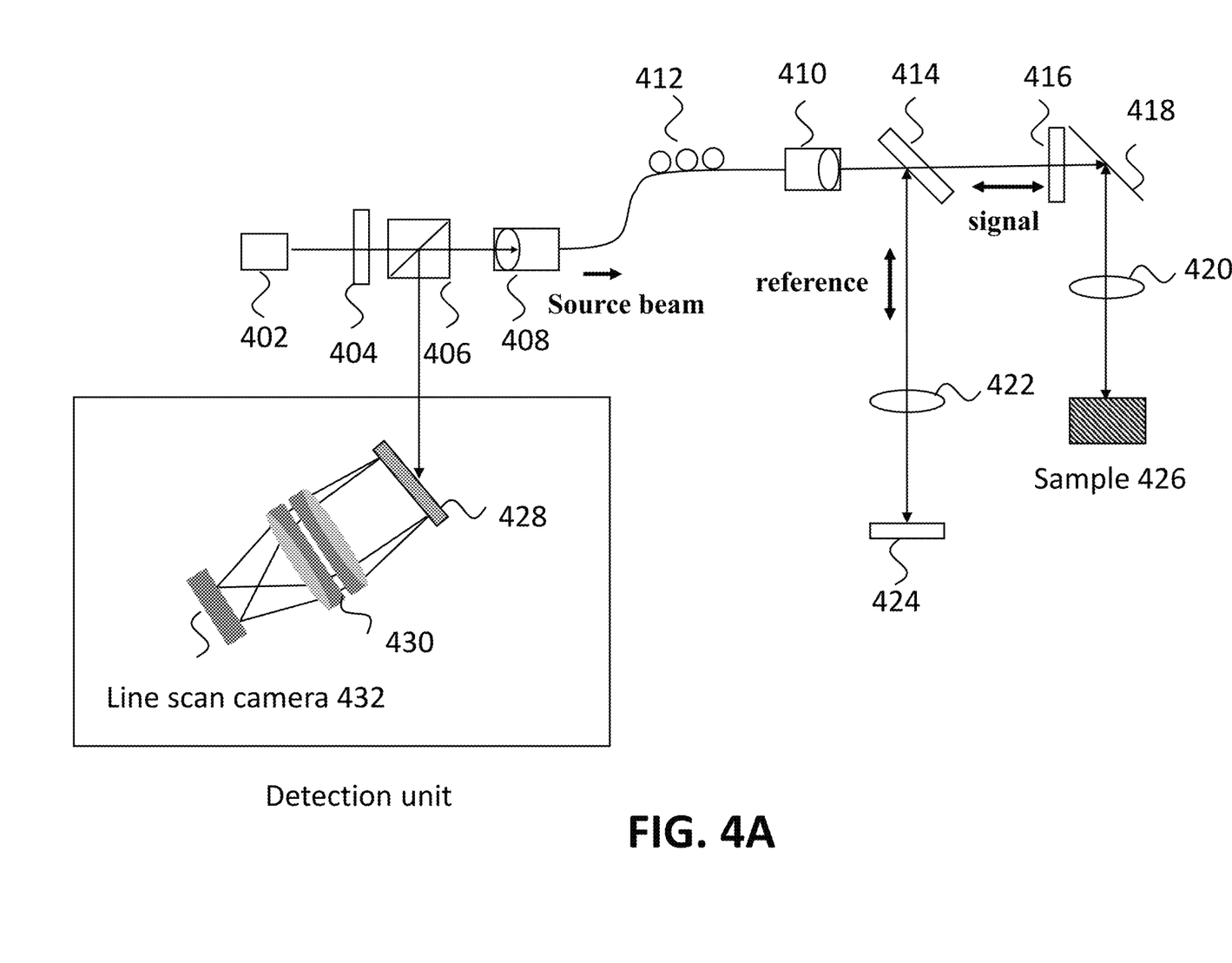
FIG. 4A is a schematic view of various hardware components of an Optical Coherence Tomography system including a light source, a polarization beam splitter, a non-polarization beam splitter, lenses, a phase mask, a half-wave plate, fiber collimator/connectors, fiber polarization controller, a mirror, and a detection unit.

An example system configured to perform an Optical Coherence Tomography scan of a sample is illustrated in FIG. 4A. Features and structures illustrated include a light source 402, half-wave plate 404 and polarization beam splitters 406, fiber collimators/connectors 408 and 410, a fiber polarization controller 412, a non-polarization beam splitter 414, a phase masks 416, a scanning mirror 418, lenses 420 and 422, a mirror 424, a grating 426, an aspherical lens pair 428 and a line scan camera 430. Embodiments of the invention may incorporate any or all of the features and structures illustrated, and may include additional features or structures not illustrated in FIGS. 4A, 4B, and 4C.

In FIG. 4A, a beam of light is generated at light source 402 using an emitter such as a superluminescent diode (SLED). The choice of an SLED light source is not intended to be limiting—any source of broad-bandwidth coherent light may be used as a light source, such as an ultrashort (femtosecond) pulsed laser emitter or supercontinuum laser emitter. Light source 402 may be coupled to computer 302 and/or a power source, such as a battery or wall outlet. The light source is incident into a single mode fiber using a half-wave plate 404 and a polarization beam splitter 406. The generated beam from the single mode fiber constitutes a "source beam," which will be split into two beams traveling along two separate paths. A first beam split from the source beam, known as the "signal beam," will be converted to an Airy beam and scanned across the sample to be imaged, as further described below. A second beam split from the source beam, known as the "reference beam," travels independently of the signal beam, and may be focused, delayed, polarized, phase modulated, and/or reflected, also as described further below. Later, the signal beam and reference beam are combined into a single "combined beam". The combined beam is guided to the detection unit by using the fiber polarization controller 412 and the polarization beam splitter 406. The detection unit consists of a grating 428, an aspherical lens pair 430, and a line scan camera 432. The combination of half-wave plate 404 and polarization beam splitter 406 can be replaced by a fiber circulator.

The source and detection use the same optical path through the single mode fiber (or fiber coupler) in FIG. 4A. The setup described in FIG. 4A is called Michelson interferometer. As further described below, in some embodiments the detection is coupled to a second single mode fiber collimator/connector forming a Mach-Zehnder interferometer. In a Mach-Zehnder interferometer, the phase modulation from the reflected sample light when re-passing the phase mask can be compensated in the reference. In some embodiments, the combination of the signal beam and reference beam may constitute a polarization-division multiplexing of the information carried by the beams. In some embodiments, prior to combination, the beams may be configured to have different polarizations so that the combined beam may be later interfered. In some embodiments, the reference beam is linearly polarized and the signal beam is circularly polarized prior to combination into the combined beam. As further described below, in some embodiments the detection unit is coupled to a second single mode fiber collimator/connector for performing fiber-based OCT.

The source beam 410 may be split using a non-polarization beam splitter, illustrated as element 414 in FIG. 4A. In some embodiments, non-polarization beam splitter 414 may be placed at a 45° angle to the light beam, which may function to split the beam into reference and signal beams. In experiments, a non-polarization beam splitter with approximately 4% reflectance was used. This is merely exemplary, and is not intended to be limiting. To reduce loss, in some embodiments the non-polarization beam splitter 414 may be treated with an anti-reflective coating that corresponds to the wavelength band of the source beam.

Once split from the source beam at the non-polarization beam splitter 414, the signal beam is directed towards and scanned across the sample 426, reflected back along a portion of its path, and combined with the reference beam prior to direction into a detection unit. A phase mask 416 is placed in the signal beam close to the scanning mirrors 418 to create Airy beam. FIG. 4A gives a basic Michelson interferometer based OCT. However, the optical design should not be limited to the free space beam splitter 414. For example, a fiber coupler can also be used for building a fiber based Michelson interferometer.

Figure 4B:
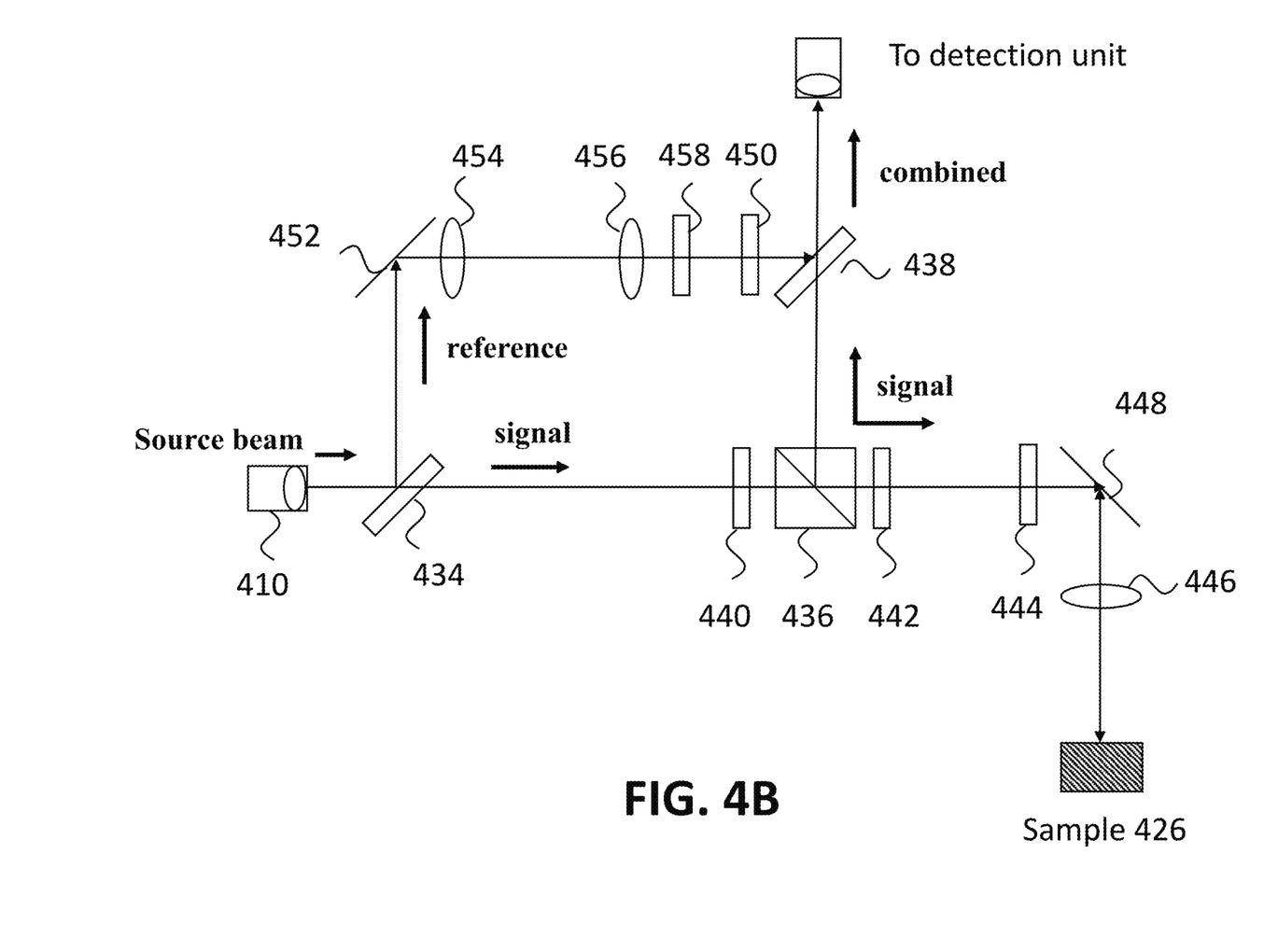
FIG. 4B is a schematic view of various hardware components of an Optical Coherence Tomography system including two non-polarization beam splitters, a polarization beam splitter, lenses, two phase masks, two half-wave plates, a quarter-wave plate, fiber collimator/connectors, and mirrors.
Figure 4C:
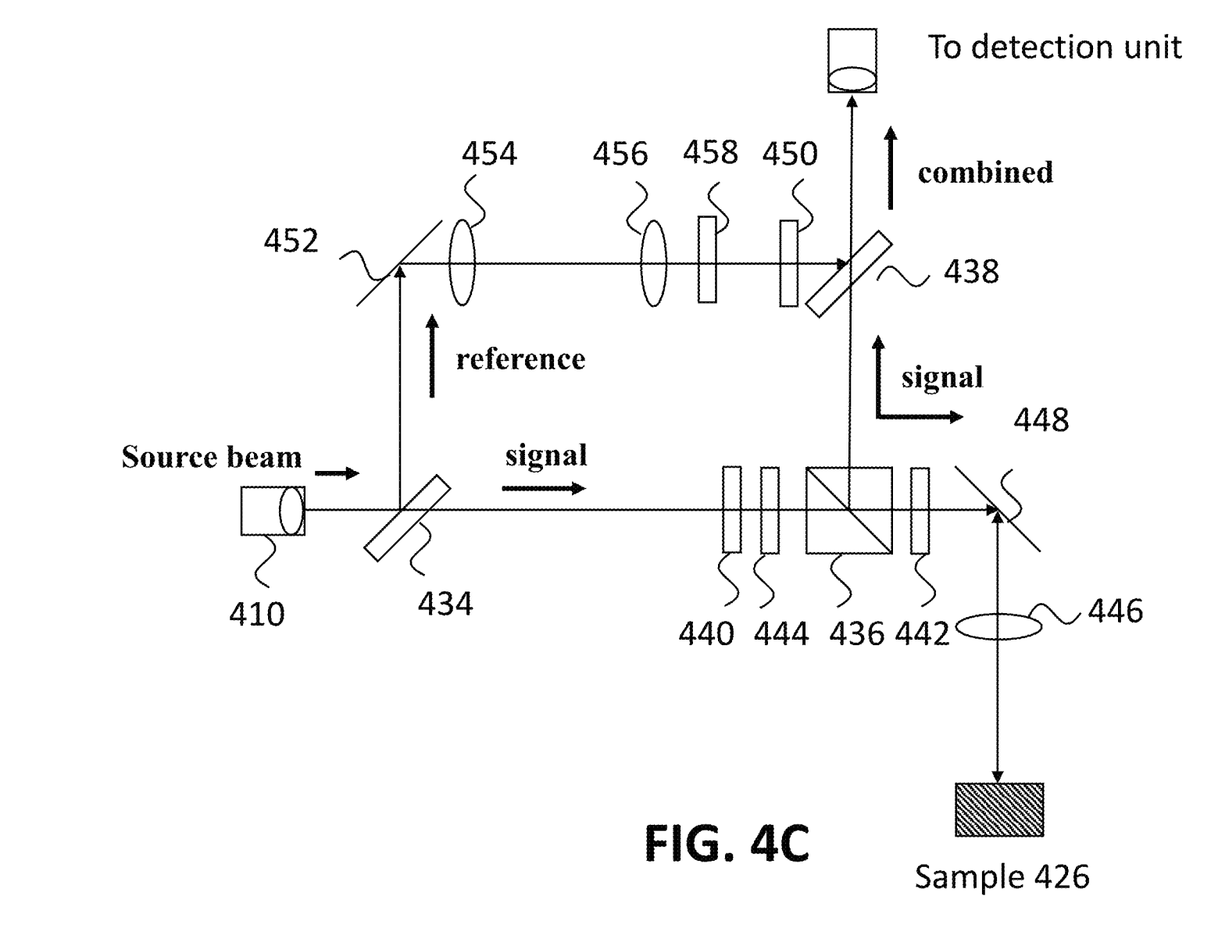
FIG. 4C is a schematic view of various hardware components of an Optical Coherence Tomography system including two non-polarization beam splitters, a polarization beam splitter, lenses, a phase mask, two half-wave plates, a quarter-wave plate, fiber collimator/connectors, and mirrors.

The detection path can be re-directed in a Mach-Zehnder interferometer in FIG. 4B. To accomplish this, a non-polarization beam splitter 434 divides the light form the source beam 410 into signal beam and reference beam. A polarization beam splitter 436 is used to selectively direct and redirect the signal beam towards either the sample or towards a second non-polarization beam splitter 438, where the signal interferes with the reference. The polarization beam splitter 436 selectively permits an incident beam of light based on the beam's polarization from the half-wave plate 440. After the polarization beam splitter 436, a quarter-wave plate 442 is used to convert the polarization of the signal beam into a circular polarization. The quarter-wave plate 442 and the polarization beam splitter 436 serve to "guide traffic" in embodiments of the system, so that the signal beam is directed towards second non-polarization beam splitter 438 only after it has been scanned and reflected from sample 426. Thus, in embodiments of the invention the combined beam from the signal and reference are re-directed to the detection unit.

In embodiments of the invention, the collimated Gaussian beam of light is converted to an Airy beam prior to being scanned across the sample 426, eliminating intensity loss due to diffraction and providing the desired increase in depth of field. Embodiments of the invention may achieve this conversion through configurations of one or more phase masks and one or more lenses.

Figure 5:
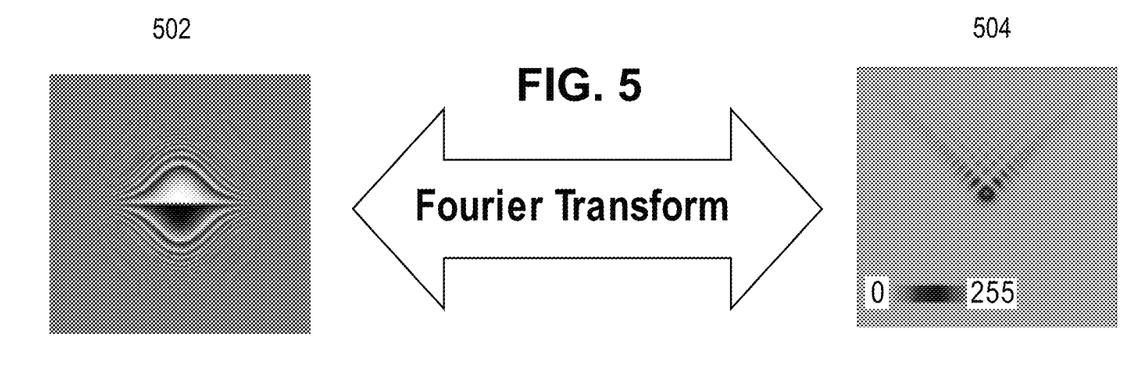
FIG. 5 is an illustration of a Fourier transformation from a phase modulated Gaussian beam to an Airy beam.

When a beam of light passes through a lens, the equation of the beam at one focus of the lens is equal to the Fourier transform of the resulting beam at the other focus of the lens. This is illustrated in FIG. 5: waveforms 502 and 504 are Fourier transforms of one another. Waveform 504 is an Airy beam waveform, while waveform 502 is its Fourier transform.

In embodiments of the invention, a signal beam is passed through a specially-designed phase mask that modulates the phase of the signal beam such that the resulting waveform of the beam is proportional to:

$$\Phi(k_\mu, k_\nu) = e^{-a(k_\mu^2 + k_\nu^2)} e^{\frac{1}{3}(k_\mu^3 + k_\nu^3)} \qquad \text{Equation 1}$$

Where α is the truncating factor with 0<α<<1. Equation 1 gives the Fourier transform of a finite energy Airy function, given by:

$$\phi(\mu,\nu,0) = Ai(\mu)Ai(\nu)e^{\alpha(\mu+\nu)} \quad 0<\alpha<<1 \qquad \text{Equation 2}$$

Figure 6:
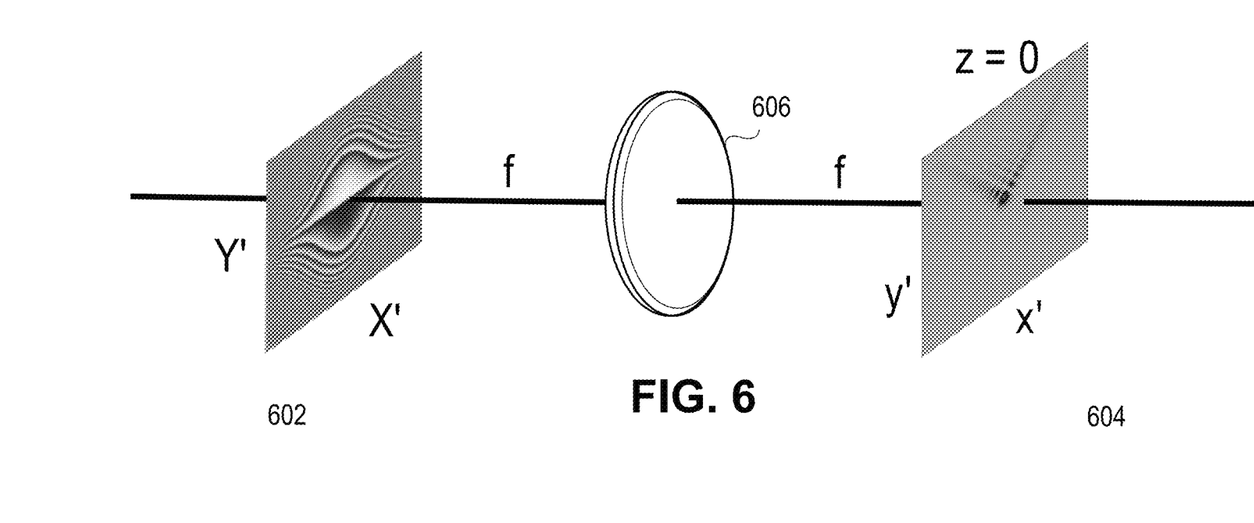
FIG. 6 is a side view of a phase modulated Gaussian beam being transformed to an Airy beam by passage through a lens.

Thus, as illustrated in FIG. 6, if the phase of a Gaussian light beam 602 is modulated at one focal point of a lens 606 to be proportional to that of the Fourier transform of a finite energy Airy beam (Equation 1), the resulting beam 604 generated at the other focus of the lens will be an Airy beam (Equation 2). The selection of the truncating factor is important to the Airy beam OCT since the truncating factor determines the energy ratio between the main lobe and side lobes. In embodiments of the invention, this is accomplished using a specially configured phase mask.

An example of a system utilizing this method is shown in FIG. 4B. A linearly polarized signal beam is converted to circular polarization by quarter-wave plate 442, as described above. The signal beam is then passed through a phase mask 444, placed close to the first focus of lens 446. This modulates the signal beam's phase to be proportional to Equation 1 at the first focal point of the lens. The signal beam then passes through lens 446, generating an Airy beam waveform at the lens's second focus. The beam is then directed towards sample 426 by scanning mirrors 448, as further described below. Upon the beam's reflection from small structures within the sample due to Mie scattering, and its subsequent return through the lens, the beam is converted back to a near plane waveform at the first focus. The beam is then passed through the phase mask and the quarter wave plate, and is directed to different path at the polarization beam splitter 436. At the second non-polarization beam splitter 438, it is combined with the reference beam for detection. In embodiments of the invention, the sample 426 is placed at the second focus of the lens 446, such that the Airy beam is generated at the surface of the sample. This placement is selected to maximize the penetration depth of the signal beam into the sample, further optimizing the depth of field of the resulting image.

Scanning mirrors 448 function to direct the signal beam towards sample 426 at two lateral directions. Over a period of time, one of the scanning mirrors scans the sample to generate an image of selected dimensions. In some embodiments, the dimensions to be scanned are selected by a user via computer 302 prior to beginning an OCT imaging process of a sample. Alternatively, in some embodiments dimensions to be scanned may be a preselected set of dimensions or may be determined automatically by computer 302.

To scan the sample, scanning mirror 448 may direct the signal beam throughout the area within the boundaries of the selected dimensions on the surface of the sample, such that the cross-sectional area of the signal beam contacts every point within the area of the sample selected to scan at least once. In this way, an area of the sample greater than the cross-sectional area of the signal beam may be imaged. In some embodiments, the scan may be configured such that the cross-sectional area of the signal beam contacts every point with the area of the sample selected to scan only once. Scanning mirrors 448 may comprise one or more mirrors driven by one or more servos coupled to a galvanometer to scan the sample. Scanning mirrors 448 may be controlled by computer 302, and may be coupled to a power source.

In embodiments of the invention, scanning mirrors 448 are placed between the first phase mask 444 and first lens 446, which operate in tandem to convert the signal beam to an Airy beam, as described above. In some embodiments, scanning mirrors 448 are placed at the focal point of the lens 446.

After being scanned across the sample 426, the signal beam is directed back towards the polarization beam splitter 436, passing through the quarter-wave plate 442. On this pass, the polarization beam splitter 446 directs the polarized sample beam towards the second non-polarization beam splitter 438 for combination with the reference beam into the combined beam.

After being split from the source beam 410 at the first non-polarization beam splitter 434, the reference beam may travel independently of the signal beam until the two are combined once again in second non-polarization beam splitter 438. In embodiments of the invention, some properties of the reference beam may be altered to intentionally differ from the signal beam (at the second non-polarization beam splitter 438). For instance, a second half-wave plate 450 may be incorporated to apply a linear polarization to the reference beam. Linear polarization of the reference beam may allow the information carried by the signal beam and reference beam to be multiplexed into the combined beam without surrendering resolvability into two distinct signals during later interference, if so desired. Further, linearly polarizing the reference beam may ensure the greatest contrast in an interference pattern created between the signal and reference beams.

Additionally or alternatively, properties of the reference beam may be altered to match those of the signal beam when the two beams are combined in the second non-polarization beam splitter 438. For instance, a second phase mask 458 may be incorporated along the reference beam's path to modulate the phase of the reference beam to equal the phase modulation of the reflected signal beam. In embodiments, the phase mask 458 should be identical to the phase mask 444.

The reference beam may be directed into the second non-polarization beam splitter 438 using one or more mirrors 452. The mirrors may be replaced by a delay line to make sure the path length matching between the signal light and reference light. Further, the reference beam may be focused by a second lens 454 and third lens 456. The focal lengths of lenses 446, 454, and 456 may be identical, in embodiments. Particularly, the second lens 454 and third lens 456 may be configured such that the optical distance between the lenses is equal to the sum of the focal lengths of the lenses. Therefore the reference beam is still collimated after the two lenses. The two-lens configuration in the reference beam is a compensation to match the double-pass of the signal beam through the lens 446.

The next embodiment of the invention only uses one phase mask. The phase mask 444 is placed before the polarization beam splitter 436 in FIG. 4C. The second phase mask is removed from the reference beam. Since the reflections form the sample do not pass through the first phase mask 444, the phase compensation is not necessary. As described above, after being scanned across a sample 426, the signal beam may pass back through the quarter-wave plate 442. The polarization beam splitter 436 reflects the signal beam towards a second non-polarization beam splitter 438 for combination with the reference beam into the combined beam.

Embodiments of the invention above have been described primarily in regards to Fourier-domain or frequency-domain OCT systems and methods.

Embodiments of the invention may alternatively operate to perform time-domain OCT by replacement of the mirror 452 with a scanned delay line, accounting for a difference in path-length traveled by the signal beam and path-length traveled by the reference beam.

Figure 7:
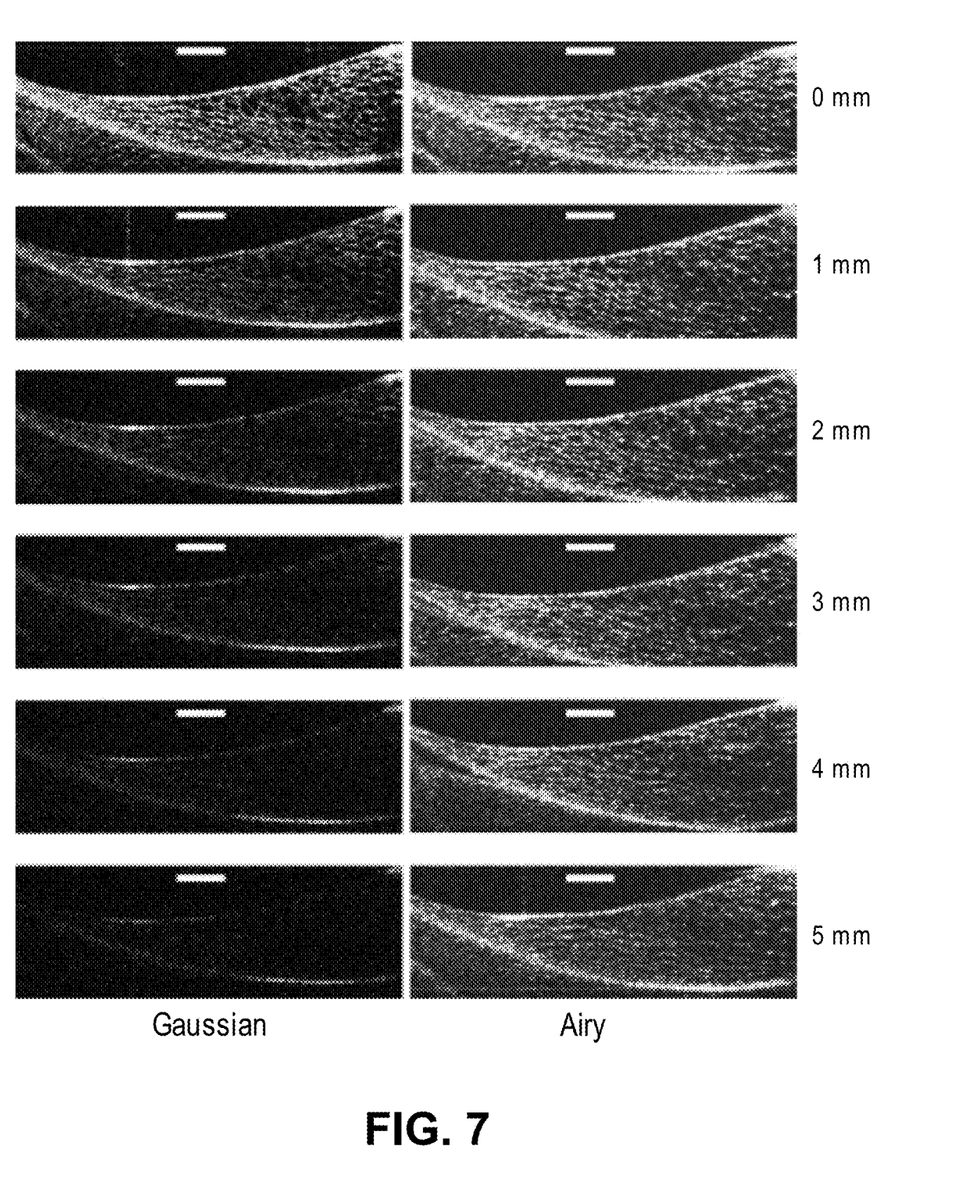
FIG. 7 is a comparison of images generated by Gaussian beam OCT with those generated using an Airy beam OCT.

FIG. 7 provides an exemplary comparison of images generated using conventional OCT techniques to those generated using an embodiment of the invention. At the surface of the sample, as indicated by the depth of 0 mm, the images generated exhibit little difference between the two imaging techniques. However, even at only a 1 mm depth, the image generated using an Airy beam in an Optical Coherence Tomography system is already clearer than that generated by conventional Gaussian beam imaging technology. This disparity increases with each increase in depth, until the image generated using conventional Gaussian beam techniques is nearly incognizable at a 5 mm depth, while the image generated using an Airy beam remains clear. At the desired 10 mm depth, the conventional OCT image would have long since faded to black, while the Airy beam image would continue to provide valuable information for study, diagnostics, and treatment of biological tissue. This FIG. 7 and description thereof is intended as illustration only and should not in any way limit embodiments of the invention.

While reference has been made above to the various components and techniques of embodiments of the invention, the description that follows will provide examples of the systems and processes of embodiments of the invention, further clarifying each feature and step. The examples below are intended to merely exemplify steps that may be taken in practice of operation of embodiments of the invention and are not intended to be limiting.

Figure 8:
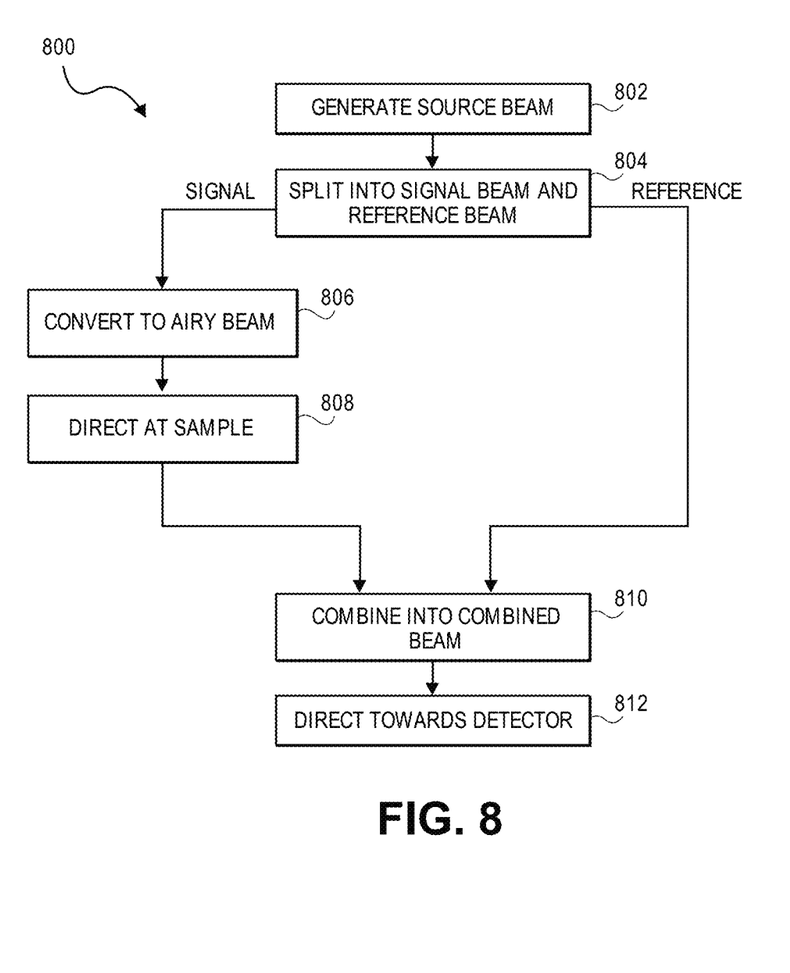
FIG. 8 is a first flow diagram of steps performed in embodiments of the invention.

FIG. 8 illustrates steps performed in operation of an embodiment of the invention, beginning with the generation and splitting of a source beam. The steps performed with a signal beam are then shown to the left of FIG. 8, while a reference beam appears to the right. The signal and reference beams are later combined and directed towards a detection unit.

First, at step 802, a source beam is generated from a light source such as an SLED, with one possible example of a light source being light source 402 from FIG. 4A. At step 804 the source beam is split into a signal beam and a reference beam. This step may be performed using a non-polarization beam splitter, as described above in reference to feature 414. At step 806, the signal beam portion is converted to an Airy beam, a process that may be accomplished by placing a phase mask 416 near one focal point of a lens 420. At step 808, the signal beam is directed at a sample, which may be organic tissue such as a human eye. The signal beam may be scanned across the sample, such that an area of the sample greater than the cross-sectional area of the signal beam may be imaged. At step 810, the signal beam and reference beam are combined into a combined beam, in some embodiments via the same non-polarization beam splitter 414. The combined beam is then directed towards a detection unit, such as a spectrometer, for detection, processing, and/or analysis in step 812.

Embodiments of the invention may perform either fiber-based OCT or free space OCT. In some embodiments, a source beam generated at light source 402 may pass through a first single mode fiber collimator/connector prior to being split into a signal beam and reference beam at first non-polarization beam splitter 414. Additionally, in some embodiments the combined beam may pass through a second single mode fiber collimator/connector prior to entering detector 326. These single mode fiber collimator/connectors are necessary for performing fiber-based OCT, but may be omitted when performing free space OCT.

Figure 9:
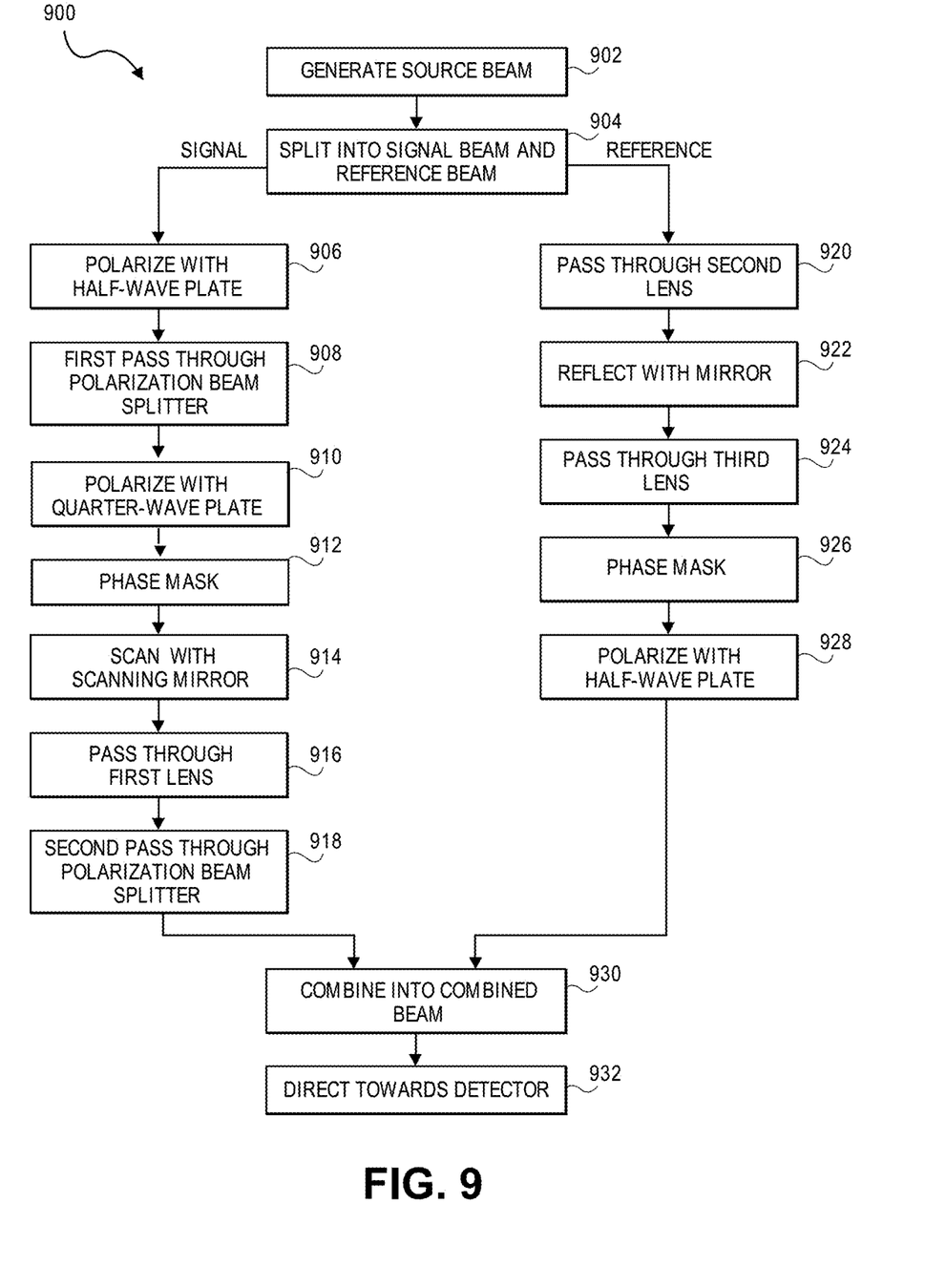
FIG. 9 is a second flow diagram of steps that may be performed in embodiments of the invention.

Further steps that may be performed in practice of some embodiments of the invention are illustrated in FIG. 9 and herein described. Like FIG. 8, FIG. 9 begins with the generation and splitting of a source beam. The steps performed with a signal beam are then shown to the left of FIG. 8, while those performed with a reference beam are to the right. Again as in FIG. 8, the signal and reference beams are later combined and directed towards a detector.

As in step 802 of FIG. 8, a source beam is generated at step 902 of FIG. 9. At step 904, the source beam is split into the above-described signal and reference beams. At step 906, the signal beam is linearly polarized using a first half-wave plate 440. Because of its linear polarization, when the signal beam encounters a polarization beam splitter 436 at step 908, it is permitted to pass through without reflection. At step 910, the signal beam passes through a quarter-wave plate 442, applying a circular polarization, a property later utilized for redirection of the beam.

At step 912, a phase modulation is applied to the signal beam via a first phase mask 444, the phase modulation corresponding to a Fourier-transformed finite energy Airy beam equation. At step 914, the polarized and phase-modulated signal beam is directed towards a sample to be imaged using scanning mirrors 448. The scanning mirror may be comprised of a first mirror driven by one or more servos coupled to a galvanometer placed at one focus of a first lens, which operates to scan the signal beam across the area of the sample for which an image is desired. After direction by the scanning mirror, the signal beam passes through a first lens 446 at step 916, functioning to Fourier transform the beam to an Airy beam at the other focus of the first lens. The sample to be imaged may be positioned such that its surface is located at this point, the second focus of the lens. Structures within 10 mm of the surface of the sample reflect the signal beam back through the first lens, scanning mirror, and phase mask. The beam then once again enters polarization beam splitter 436, but this time is reflected away from the source beam channel and towards second non-polarization beam splitter 438 due to the rotation of signal beam's polarization by the quarter-wave plate 442.

Meanwhile, at step 920, the reference beam passes through a second lens 454, focusing the beam, and is reflected towards a third lens 456 using a mirror 452 at step 922. At step 924 the reference beam passes through the third lens, which may be positioned such that the optical distance between the second and third lens is equal to the sum of their respective focal lengths. The reference beam will be collimated after this two-lens configuration, as well as be matched with the signal beam through the first lens (step 916). At step 926 the reference beam passes through a phase mask, providing phase modulation on a collimated beam. Next, the reference beam is linearly polarized using a second half-wave plate at step 928 so that the reference beam's contribution to the combined beam may be easily extracted later from the polarized contribution from the signal beam. At step 930, the signal and reference beams are combined into a single combined beam, which (as in step 812 of FIG. 8) is directed towards a detection unit at step 932. The detection unit may be, for instance, a spectrometer. This is not intended to be limiting. The detected signal may then be processed by computer 302 in FIG. 3, in some embodiments through operation of graphics processing unit 312. An image generated may be displayed on monitor 316 for analysis, review, or manipulation, and may be stored in local storage 322. The steps in FIG. 9 can be modified with placing the first phase mask 444 before the polarization beam splitter 436 while removing the second phase mask 458 in the reference.

Because embodiments of the invention incorporate a collimated laser beam, some applications may observe a speckle pattern caused by the mutual interference of reflected wavefronts from an imaged sample. While speckle phenomena may be deleterious to the resultant image in some applications, in others the speckle may be advantageously analyzed to collected information about the imaged sample.

In some embodiments of the invention, a spatial light modulator may be incorporated to allow for observation and/or control of imaged speckle arising from the structured light collimated laser beam passing through a diffuser and reflecting from the imaged sample. The spatial light modulator may comprise a commercial projector and an adjustable-width aperture may be incorporated to finely tune the speckle pattern produced. In embodiments of the invention, the spatial light modulator may be adjusted in response to a first generated image in order to increase or reduce a produced speckle pattern. Particularly, the width of the adjustable-width aperture may be increased or decreased to adjust the resulting speckle pattern. In other embodiments, the spatial light modulator may be adjusted prior to any measurement being performed.

It should be appreciated that, while the above disclosure is directed mainly to the field of medical imaging, some embodiments of the invention may be employed for any pursuit that could be furthered by Optical Coherence Tomography. Embodiments of the invention may be used in any setting or field, such as art restoration, forensics, or archaeology to produce an image of a sample with an increased depth of field. The medical diagnostics field discussed is merely exemplary and should not be construed as limiting.

Having thus described various embodiments of the invention, what is claimed as new and desired to be protected by Letters Patent includes the following:

1. An Optical Coherence Tomography system comprising:
    a source beam;
    a first non-polarization beam splitter;
    wherein said first non-polarization beam splitter splits said source beam into a signal beam and a reference beam;
    a polarization beam splitter;
    a first phase mask and a first lens to convert said signal beam into an Airy beam;
    a scanning mirror between said first phase mask and said first lens; and
    a second non-polarization beam splitter to combine said signal beam and said reference beam into a combined beam.

2. The system of claim 1, wherein said scanning mirror comprises at least one mirror driven by one or more servos coupled to a galvanometer.

3. The system of claim 1, additionally comprising a detection unit receiving said combined beam.

4. The system of claim 1, further comprising:
    a first half-wave plate to polarize said signal beam prior to a first passage through said polarization beam splitter; and
    a quarter-wave plate to repolarize said signal beam prior to a second passage through said polarization beam splitter.

5. The system of claim 1, further comprising:
    a second phase mask to modulate a phase of said reference beam; and
    a second half-wave plate to polarize said reference beam.

6. The system of claim 1, wherein said source beam is generated by a superluminescent diode.

7. The system of claim 1, additionally comprising a delay line delaying said reference beam.

8. The system of claim 1, additionally comprising a second mirror reflecting said reference beam.

9. The system of claim 8, additionally comprising a second lens and a third lens focusing said reference beam.

10. The system of claim 9, wherein an optical distance between said second lens and said third lens is equal to a sum of a focus distance of said second lens and a focus distance of said third lens.

11. The system of claim 1, additionally comprising one or more single mode fiber collimator/connectors.

12. The system of claim 1, wherein said first phase mask is placed at or near a first focus of said first lens.

13. The system of claim 1, wherein a sample is placed at a second focus of said first lens.

14. The system of claim 1, wherein said first and second non-polarization beam splitters are treated with an anti-reflective coating corresponding to a wavelength band of the source beam.

15. A method of performing Optical Coherence Tomography on a sample, the method including the steps of:
    generating a source beam;
    splitting said source beam into a signal beam and a reference beam using a non-polarization beam splitter;
    converting said signal beam into an Airy beam using a first lens;
    directing said signal beam towards the sample using a scanning mirror;
    focusing said reference beam using a second lens and a third lens;
    combining said signal beam and said focused reference beam into a combined beam using the non-polarization beam splitter; and
    directing said combined beam towards a detector.

16. The method of claim 15, wherein said detector comprises a grating, an aspherical lens pair, and a line scan camera.

17. The method of claim 15, further including the step of processing said combined beam using a graphics processing unit.

18. A system for performing Optical Coherence Tomography on a sample, the system comprising:
    a source beam;
    a first non-polarization beam splitter;
    wherein said first non-polarization beam splitter splits said source beam into a signal beam and a reference beam;
    a polarization beam splitter;
    a first half-wave plate to polarize said signal beam prior to a first passage through said polarization beam splitter;
    a first phase mask and a first lens to convert said signal beam into an Airy beam;
    a scanning mirror comprising a first mirror driven by one or more servos coupled to a galvanometer;
    wherein said scanning mirror is configured to direct said signal beam towards a sample;
    a quarter-wave plate to repolarize said signal beam prior to a second passage through said polarization beam splitter;
    a second half-wave plate to polarize said reference beam; and
    a second non-polarization beam splitter to combine said signal beam and said reference beam into a combined beam and direct the combined beam towards a detector.

19. The system of claim 18, additionally comprising a second lens and a third lens focusing said reference beam, wherein an optical distance between said second lens and said third lens is equal to a sum of a focus distance of said second lens and a focus distance of said third lens.

20. The system of claim 18, additionally comprising a second phase mask to modulate a phase of said reference beam prior to polarization of said reference beam.

* * * * *